US009655779B2

(12) United States Patent
Bigler et al.

(10) Patent No.: US 9,655,779 B2
(45) Date of Patent: May 23, 2017

(54) APPARATUS AND METHODS FOR TREATING EXCESS INTRAOCULAR FLUID

(71) Applicant: ÉCOLE POLYTECHNIQUE FÉDÉRALE DE LAUSANNE, Lausanne (CH)

(72) Inventors: Stéphane Bigler, Leysin (CH); Nikolaos Stergiopulos, Préverenges (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 0 days.

(21) Appl. No.: 14/819,286

(22) Filed: Aug. 5, 2015

(65) Prior Publication Data
US 2015/0335488 A1  Nov. 26, 2015

Related U.S. Application Data

(63) Continuation of application No. 13/349,353, filed on Jan. 12, 2012, now Pat. No. 9,101,445.
(Continued)

(51) Int. Cl.
*A61M 9/00* (2006.01)
*A61F 9/007* (2006.01)
(Continued)

(52) U.S. Cl.
CPC .......... *A61F 9/00781* (2013.01); *A61F 9/00* (2013.01); *A61F 9/0008* (2013.01);
(Continued)

(58) Field of Classification Search
CPC ...... A61M 1/1039; F04B 43/04; F04B 43/043; F04B 43/08; F04B 43/082; F04B 43/09; F04B 43/12
See application file for complete search history.

(56) References Cited

U.S. PATENT DOCUMENTS

| 3,863,067 A | 1/1975 | Gooley |
| 4,232,451 A | 11/1980 | Thomsen |

(Continued)

FOREIGN PATENT DOCUMENTS

| EP | 1 243 826 A2 | 9/2002 |
| EP | 1 484 535 A1 | 12/2004 |

(Continued)

OTHER PUBLICATIONS

International Search Report & Written Opinion dated Mar. 29, 2012 in Int'l PCT Patent Application No. PCT/EP2012/050455.

*Primary Examiner* — Leslie Deak
*Assistant Examiner* — Kai Weng
(74) *Attorney, Agent, or Firm* — Foley & Lardner LLP; Christopher C. Bolten; Nicola A. Pisano

(57) ABSTRACT

An ocular drainage system is provided for treating diseases that produce elevated intraocular pressures, such as glaucoma, wherein the system includes an implantable device and an external control unit. The implantable device includes a non-invasively adjustable valve featuring at least one deformable tube and a disk rotatably mounted within a housing, such that rotation of the disk using the external control unit causes the disk to apply a selected amount of compression to the deformable tube, thereby adjusting the fluidic resistance of the deformable tube and regulating the intraocular pressure.

19 Claims, 8 Drawing Sheets

Related U.S. Application Data

(60) Provisional application No. 61/433,131, filed on Jan. 14, 2011.

(51) Int. Cl.
 *A61F 9/00* (2006.01)
 *A61M 27/00* (2006.01)
 *A61M 1/10* (2006.01)
 *F04B 43/04* (2006.01)

(52) U.S. Cl.
 CPC ........ *A61F 9/00736* (2013.01); *A61M 1/1037* (2013.01); *A61M 27/002* (2013.01); *F04B 43/04* (2013.01)

(56) References Cited

U.S. PATENT DOCUMENTS

| | | | |
|---|---|---|---|
| 4,457,757 A | 7/1984 | Molteno | |
| 4,856,972 A * | 8/1989 | Van Benschoten | F04B 43/12 417/477.1 |
| 5,117,870 A | 6/1992 | Goodale et al. | |
| 5,300,020 A | 4/1994 | L'Esperance, Jr. | |
| 5,342,025 A | 8/1994 | Hwang | |
| 5,411,473 A | 5/1995 | Ahmed | |
| 5,586,872 A | 12/1996 | Skobelev et al. | |
| 5,601,094 A | 2/1997 | Reiss | |
| 5,626,558 A | 5/1997 | Suson | |
| 6,050,970 A | 4/2000 | Baerveldt | |
| 6,077,299 A | 6/2000 | Adelberg et al. | |
| 6,168,575 B1 | 1/2001 | Soltanpour | |
| 6,186,974 B1 | 2/2001 | Allan et al. | |
| 6,261,256 B1 | 7/2001 | Ahmed | |
| 6,450,984 B1 | 9/2002 | Lynch et al. | |
| 6,508,779 B1 | 1/2003 | Suson | |
| 6,589,198 B1 | 7/2003 | Soltanpour et al. | |
| 6,726,664 B2 | 4/2004 | Yaron et al. | |
| 7,093,818 B2 | 8/2006 | Koeneman | |
| 7,854,600 B2 | 12/2010 | Ogawa | |
| 2005/0053501 A1 | 3/2005 | Akahori | |
| 2007/0154336 A1* | 7/2007 | Miyazaki | A61M 5/14228 417/474 |
| 2009/0099626 A1 | 4/2009 | De Juan et al. | |
| 2009/0208350 A1 | 8/2009 | Miyazaki et al. | |
| 2010/0321345 A1 | 12/2010 | Pearce et al. | |
| 2011/0066098 A1 | 3/2011 | Stergiopulos | |

FOREIGN PATENT DOCUMENTS

| | | |
|---|---|---|
| JP | 54-007791 | 1/1979 |
| WO | WO-93/03778 A1 | 3/1993 |
| WO | WO-96/03944 | 2/1996 |
| WO | WO-99/62586 | 12/1999 |
| WO | WO-99/66862 | 12/1999 |
| WO | WO-2009/066133 A1 | 5/2009 |

* cited by examiner

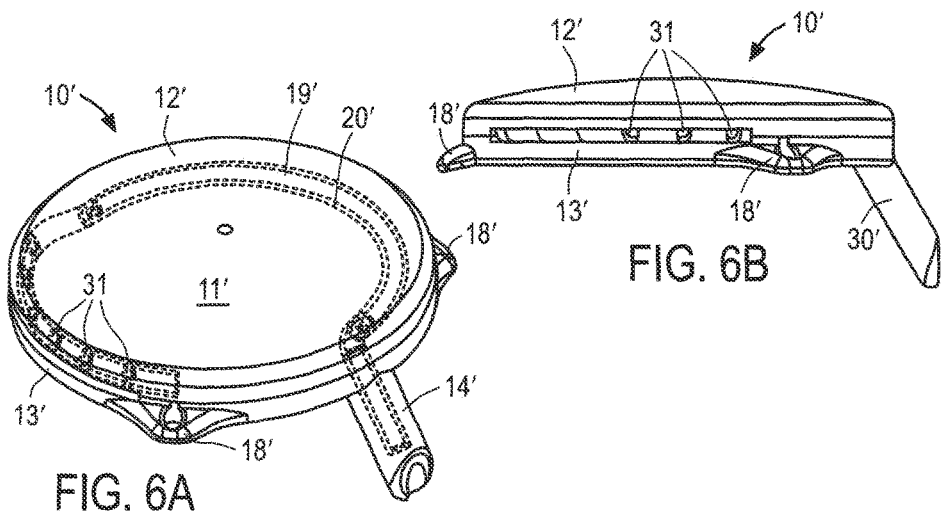
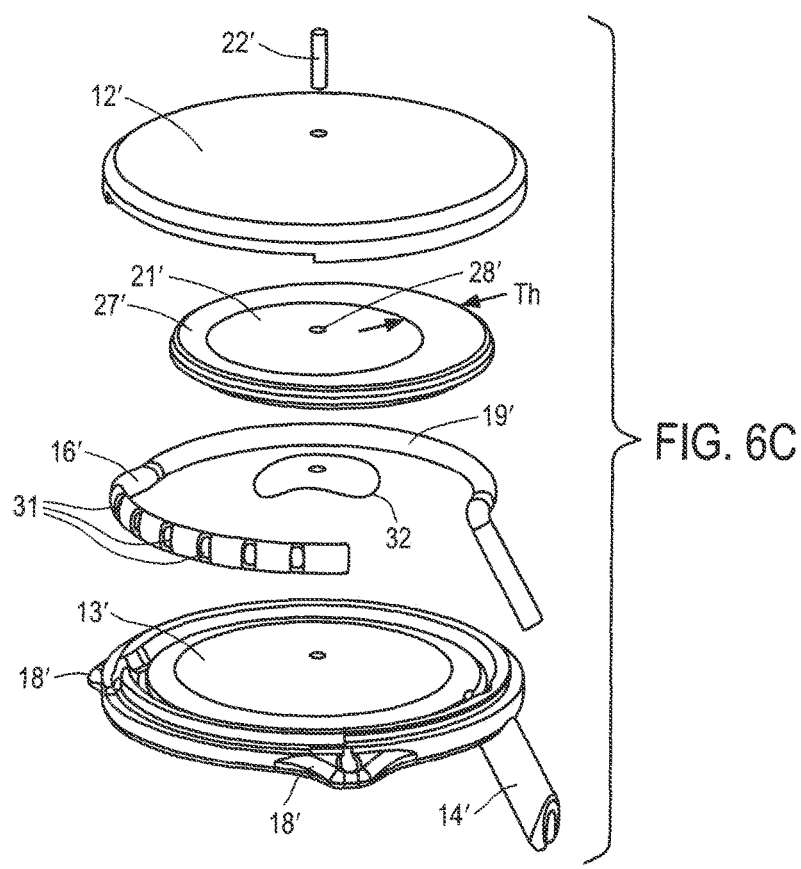

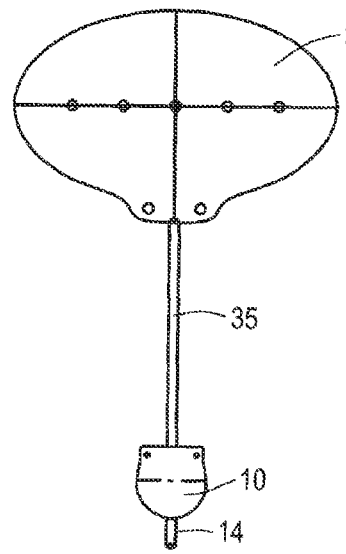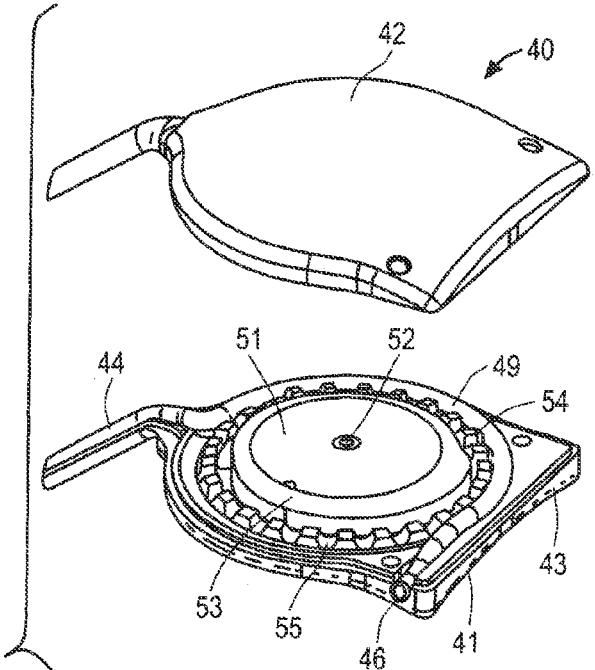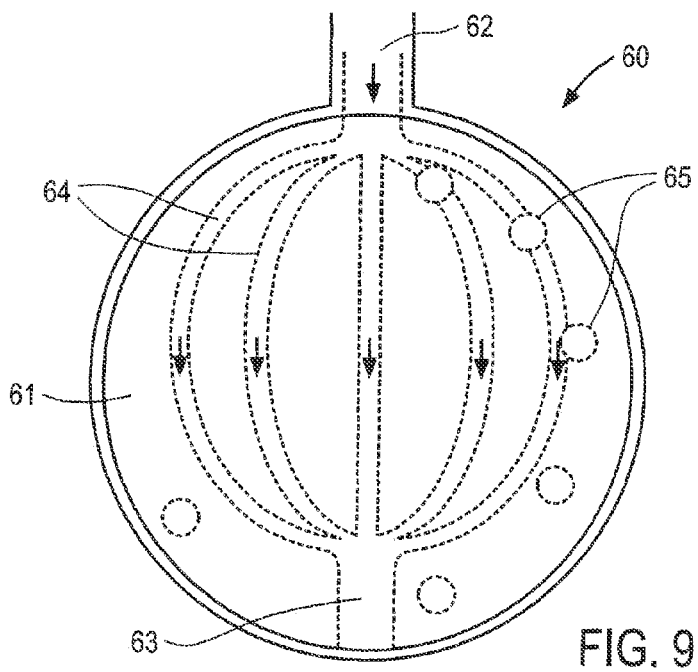

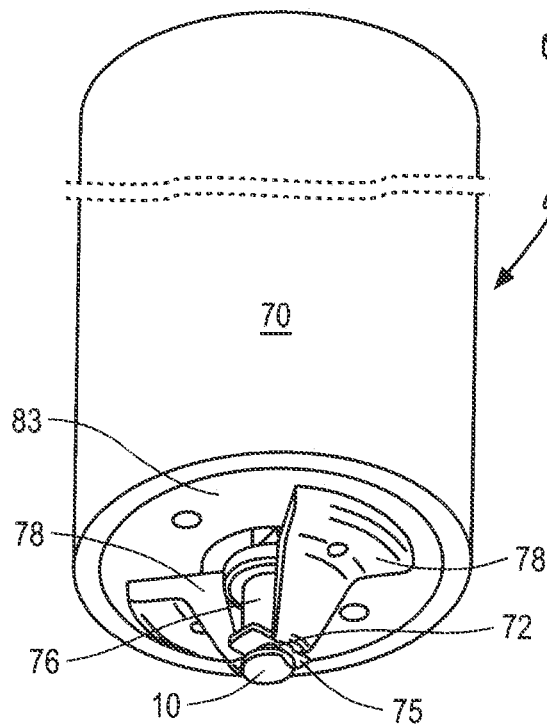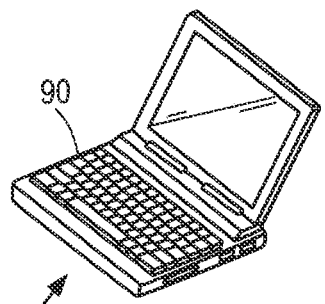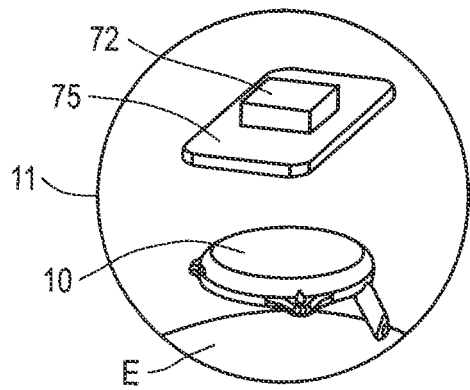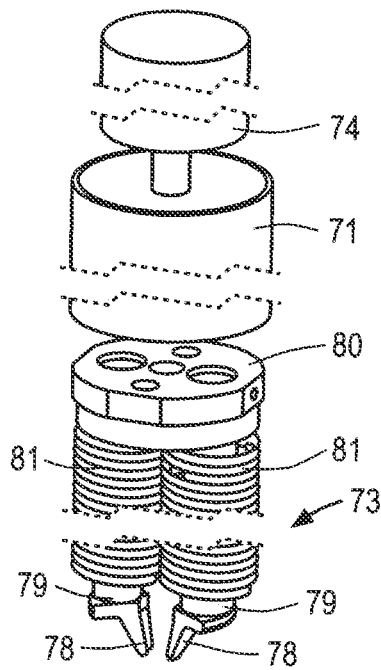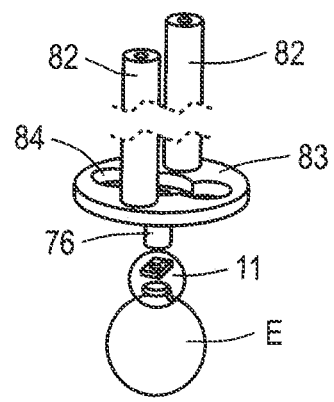
FIG. 10A
FIG. 10B
FIG. 11

APPARATUS AND METHODS FOR TREATING EXCESS INTRAOCULAR FLUID

I. CROSS-REFERENCE TO RELATED APPLICATIONS

This application is a continuation application of U.S. application Ser. No. 13/349,353, filed Jan. 12, 2012, now U.S. Pat. No. 9,101,445, which claims the benefit of priority of U.S. Provisional Application No. 61/433,131, filed Jan. 14, 2011, the entire contents of each of which are incorporated by reference.

II. FIELD OF THE INVENTION

This application relates to apparatus and methods for draining excess intraocular fluid, for example, resulting from glaucoma.

III. BACKGROUND OF THE INVENTION

Glaucoma affects about 70 million people worldwide, and is a disorder associated with high pressure in the eye resulting in the generation of excess intraocular fluid (aqueous humor). Aqueous humor is produced at a rate of 2-3 μl/min by the ciliary body and it maintains constant intraocular pressure (IOP) around 12-20 mm Hg. Aqueous humor exits the eye primarily through the trabecular meshwork and Schlemm's canal, where it eventually drains to the episcleral veins. Maintaining intraocular pressure within appropriate ranges is critical to health of the eye, and depends on aqueous hunter dynamics, namely the production rate from the ciliary body (aqueous humor inflow) and its outflow rate through the trabeculum. The most frequent glaucoma is called open-angle glaucoma, and results from an increase in the fluidic resistance of the trabecular meshwork. Left untreated, this disease typically causes damage to the optic nerve, with consequent loss of vision, initially peripheral, but progressively leading to total blindness. Unfortunately, glaucoma is often asymptomatic until late in the progress of the disease.

Traditionally, glaucoma is treated using medication, for example, the daily application of eye drops, such as Brinzolamide ophthalmic, that reduce production of aqueous humor. Such medications do not cure glaucoma, and must be continue to be taken to maintain intraocular pressures within accepted limits. In certain cases, such treatment may fail and other surgical treatments are employed, such as filter procedures or placement of a glaucoma drainage device. Glaucoma drainage devices reduce intraocular fluid pressure by providing an artificial drainage pathway, thus maintaining a low intraocular pressure ("IOP").

Previously-known glaucoma drainage devices usually comprise a structure having a drainage tube that is inserted through a small incision made in the conjunctiva. The surgeon then makes a tiny incision in the sclera of the eye and creates an opening for the drainage implant device. The drainage tube is placed such that the opening of the tube is disposed in the anterior chamber of the eye within the aqueous humor. The tube is sutured in place with the drainage device attached to the sclera of the eye. Many surgeons will place an absorbable suture around the tube at the time of surgery to prevent overfiltration through the device until a fibrous capsule has formed. Accordingly, such devices typically are not functional until about 3 to 8 weeks after the procedure, so as to prevent over-filtration.

An exemplary previously-known passive glaucoma drainage device is described in U.S. Pat. No. 4,457,757 to Molteno. The device described in that patent comprises a tube of a biologically inert silicone configured to be inserted into the eye to drain aqueous humor from the anterior chamber of the eye. The device does not include a pressure regulating mechanism, but instead relies on the resistance to aqueous flow through the tubing to prevent over drainage.

One drawback of devices such as those described in the Molteno patent is that the drainage flow depends on IOP and on the fixed hydrodynamic resistance of the shunt. In many cases, however, the hydrodynamic resistance of the shunt may not be sufficient to reduce high IOP when the resistance to flow is too high, or may lead to over-drainage if the resistance is low. For example, a common problem, which arises shortly after implantation, is hypotony, which occurs when IOP drops below acceptable physiological levels (i.e., IOP<10 mmHg). Hypotony usually takes place the first few days to weeks following the implantation of a glaucoma drainage device, and is a combined result of a low fluidic resistance of both the implant and the distal outflow paths. Hypotony may lead to a number of undesirable effects and complications, such as hypotensive maculopathy, cataract formation and optic nerve edema. Another problem, also related to the fixed fluid resistance of previously known implants, is fibrosis, which appears progressively at long term and which, depending on its extend and severity, may raise the effective fluidic resistance of the implant, thereby raising the IOP to different, often non-physiological, levels.

The foregoing drawbacks have been recognized in the prior art, and several improvements have been attempted to improve flow control over the entirely passive system described in Molteno.

For example, U.S. Pat. No. 5,411,473 to Ahmed describes is drainage device that includes membrane-type valve. More specifically, Ahmed describes a drainage system including a membrane folded and held in tension between two plates to provide a slit opening, such that the membrane responds to pressure changes to open or close the slit opening. Unfortunately, the operational characteristics of the system depend on the properties of the membrane, which cannot be changed easily once the device is implanted.

U.S. Pat. No. 5,300,020 to L'Esperance also describes a drainage system having a flow control element. In this patent, flow is controlled by a plug of absorbable material having porous properties that maintains anterior chamber pressure. Once aqueous humor has been absorbed into the plug, a path of relatively slow drainage flow will be established into the subconjunctival space until an equilibrium of pressures is developed. The pressure release is slow enough to avoid a collapse of the cornea yet sufficient to lower the intraocular pressure. Like the system described in Ahmed, the device described in L'Esperance includes the disadvantage that the porous material has fixed flow characteristics, and cannot be changed adapt to changes in the progression of the disease.

L'Esperance describes a further embodiment comprising a flexible drainage tube with a time-delay valve structure. The valve includes a ball biocompatible absorbable material that squeezes a portion of the drainage tube closed. As the absorbable material is dissolved by the aqueous humor, the squeezing force applied by the ball drops, progressively reducing the flow resistance of the drainage tube. In yet another embodiment, the time-delay valve comprises polymer components that either inherently, or due to the choice of composition, selectively shrink or stretch to effect opening and/or closure operation of the valve. In both of these latter embodiments, precise adjustment of the drainage flow rate is difficult to achieve, and once the valve control component has dissolved or changed shape further flow regulation is not possible.

Still other examples of previously-known systems are known. U.S. Pat. Nos. 5,626,558 and 6,508,779 to Suson describe a shunt which may be adjusted after implantation by using a low power laser to drill additional openings in the tube wall to adjust the flow rate. U.S. Pat. No. 6,186,974 to Allan et al. describes a drainage shunt having multiple layers, one of which may be a gel that swells upon absorption of fluid to adjust flow rate through the tube. U.S. Pat. No. 6,726,664 to Yaron describes a drainage tube including a distal hook that retains the distal end of the implant within the anterior chamber of the eye, and various means, such as rods or sutures, for partially occluding the lumen of the tube to regulate flow.

Other previously-known glaucoma treatment systems include significantly greater complexity to address the drawbacks of the simpler shunt systems described above. For example, U.S. Pat. No. 6,077,299 to Adelberg, et al. describes a non-invasively adjustable valved implant for the drainage of aqueous humor in glaucoma, wherein an implant having an inlet tube is surgically inserted in the anterior chamber of the eye to allow aqueous humor to flow from the anterior chamber to a valve. After passing through a pressure and/or flow regulating valve in the implant, the fluid is dispersed along the periphery of the implant to the interior of the Tenon's capsule where it is absorbed by the body. In one embodiment, the valve inhibits flow below, and allows flow above, a specific pressure difference between the intraocular pressure within the eye and the pressure within the bleb cavity in the Tenon's capsule. The specified pressure difference or set-point is always positive and the valve is always closed in the presence of negative pressure differences, to prevent reverse flow of fluid from the Tenon's capsule back into the anterior chamber of the eye.

In Adelberg, the valve is formed by a chamber to which the inlet tube is connected, such that the chamber is closed by a pressure sensitive valve in the shape of a flat cone. The pressure regulation set point of the valve is governed by a flexible diaphragm that cooperated with an armature plate having an inclined surface, and which is configured to slide over a complementary inclined surface attached to the diaphragm. Cooperation of the inclined surface of the plate and the complementary surface causes the diaphragm to deflect depending on where the armature plate is located. The armature plate is rotated, using a rotor and a set of speed-reducing and torque-enhancing gears, to regulate the flow through the device. The characteristics of the valve strongly depend on the configuration of the cone shaped valve. In addition, the regulating mechanism is complex, including many rotating parts and gears, and this complexity poses a risk of malfunction.

U.S. Pat. Nos. 6,168,575 and 6,589,198 to Soltanpour et al. describe micro-pump assemblies that may be implanted in the eye for controllably removing excess fluid to treat glaucoma. In these patents, the implantable pumps have a variable pumping rate that may be adjusted either manually or automatically, controlled by the measured intra-ocular pressure. However, these devices have the disadvantage of being complicated and expensive. In addition, because the implantable device contains electronics and a power source, such elements must be miniaturized to fit within in a suitably small sealed enclosure. As for the device described in Adelberg, the risk of malfunction also is high due to the large number of interacting elements present that must cooperate together.

Finally, WO 2009/066133 describes an ocular drainage system including a hollow chamber coupled to a drainage tube and a disk disposed within the hollow chamber. Flow from an exit hole of the drainage tube into the hollow chamber is controlled by rotating the disk to align a variable section slit on the disk with the exit hole. Fluid passing through the exit hole and the variable section slit into the hollow chamber is released outside of the implant. Flow through the device is adjusted by magnetically coupling an external adjustment device to the disk, which enables the disk to be rotated non-invasively. A drawback of the system described in this publication, however, is that large torques may be required to rotate the disk within the hollow chamber after implantation, due to deposit of proteinaceous materials from the aqueous humor.

In view of the drawbacks of the foregoing prior at devices and methods, it would be desirable to provide an ocular drainage system and methods that are capable of being non-invasively adjusted after implantation to control the hydraulic resistance of the device.

It further would be desirable to provide an ocular drainage system having few moving parts, thereby enhancing robustness of the system and reducing the risk of failure arising from having many complex, interacting parts.

It further would be desirable to provide an ocular drainage system and methods wherein moving parts of the system are configured to reduce the risk of clogging or becoming inoperative due to the buildup of proteinaceous sediments.

Finally, it would be desirable to provide an ocular drainage system and methods that permits the hydraulic resistance of the system to be periodically adjusted in a non-invasive manner.

IV. SUMMARY OF THE INVENTION

The present invention overcomes the drawbacks of previously-known ocular drainage systems by providing an implantable device having few moving parts, and which may be non-invasively periodically adjusted to control the fluidic resistance of the device, thereby avoiding hypotony and enabling intraocular pressure to be maintained within desired limits over extended periods. In addition, the ocular drainage device of the present invention is configured so as to minimize buildup of proteinaceous sediment from the aqueous humor on moving parts of the device, thereby ensuring that the implantable device remains functional and adjustable over extended periods.

The foregoing advantages a achieved by providing an ocular drainage system comprising an implantable device and an external control unit. The implantable device includes a non-invasively adjustable valve comprising a housing that encloses at least one deformable tube and a disk rotatably mounted within the housing. The housing includes an inlet port that communicates with the anterior chamber of the eye and an outlet port that permits aqueous humor entering the valve via the inlet port to be deposited within, e.g. as bleb firmed in the sclera or a glaucoma drainage device in the form of a Seton tube, such as a Baerveldt or a Molteno device.

In accordance with one aspect of the present invention, an edge of the disk bears against the drainage tube, so that a selected degree of compression may be applied to the drainage tube depending upon the extent of rotation of the disk. In one embodiment, the disk is eccentrically mounted, comprises a magnetic material or magnetizable metal alloy, and is manipulated non-invasively using the external control unit, which may comprise permanent magnets or an electromagnet. The disk preferably includes one or more ball bearings to reduce the torque required to rotate the disk after implantation. The disk optionally may include a feature that locks the disk in position to prevent inadvertent movement e.g., due to shock, and requires the application of a minimum threshold torque to adjust the rotation of the disk.

In preferred embodiments of the ocular drainage system of the present invention, the housing and disk are curved to accommodate the curvature of the eye, thereby permitting the device to be implanted under a flap formed in the sclera. In addition, the housing may include spaces that accept portions of the drainage tube(s) when the disk is rotated to compress the drainage tube to adjust flow through the device. The deformable tube may extend from the inlet port to the outlet port of the housing, or alternatively, may extend within the housing over the useful arc of contact with the disk. The outlet port may include a single or multiple openings through which fluid may exit the implantable device to the exterior of the eye. As an alternative, a plurality of deformable tubes may be used within the housing, so that rotation of the disk within the implantable device selectively and reversibly closes off a corresponding subset of the plurality of tubes.

In accordance with another aspect of the present invention, an external control unit is provided that enables the implantable device to be non-invasively adjusted. In one embodiment, the control unit comprises a sensor for detecting the current orientation of the disk disposed within the implantable device, and one or more magnets that magnetically coupled with the disk to cause the disk to rotate through a selected angle to adjust the fluidic resistance of, and thus flow through, the device. Preferably, the magnets employed in the control unit are electromagnets, and the control unit includes, or can be coupled to, a display that provides a visual confirmation of the degree of adjustment of the implantable device.

In an alternative embodiment, the disk is mounted concentrically within the housing and includes a variable thickness rim that forms a cam surface configured to bear against a plurality of movable pins that selectively contact and compress the deformable tube responsive to a selected angular orientation of the cam surface. In yet further embodiments, the disk may be concentrically mounted within the housing and disposed above the deformable tube, which may include a network of connected tubes. A lower surface of the disk includes a plurality of protrusions that selectively contact and compress individual ones of the tubes within the network to increase fluidic resistance through the network responsive to a selected angular orientation of the disk.

In still other alternative embodiments, the disk may include circuitry for inducing a local magnetic field in the disk that is out of phase with the magnetic field applied by the control unit. In this configuration, the magnetic field applied by the control unit may be steered to induce a desired degree of rotation of the disk within the implantable device. In another alternative embodiment, the implantable device may be configured as an ultrasonic motor, and the control unit may be coupled ultrasonically to the implantable device, rather than employing magnetic coupling to rotate the disk.

Methods of implanting and operating the ocular drainage system of the present invention also are provided.

V. BRIEF DESCRIPTION OF THE DRAWINGS

FIGS. 1A, 1B and 1C are, respectively, a perspective view an exemplary implantable device of the ocular drainage system of the present invention depicting internal components of the device in a see-through housing (FIG. 1A), illustrating the route of an adjustable fluid path within the housing (FIG. 1B), and illustrating an exploded perspective view depicting the components of the implantable device (FIG. 1C).

FIGS. 6A, 6B and 6C are, respectively, a perspective view and side view of an alternative embodiment of an exemplary implantable device of the ocular drainage system of the present invention depicting a fluid path, and an exploded perspective view depicting the components of that implantable device.

FIG. 7 is a plan view of an implantable device of the present invention including a in-series connection to a Seton tube.

FIG. 8 is another exemplary embodiment of the implantable device of the present invention in which fluidic resistance is controlled by a cam-shaped concentrically mounted disk that acts through a plurality of movable pins.

FIG. 9 is a further exemplary embodiment of the implantable device of the present invention in which the deformable tube comprises a network of interconnected tubes that are selectively compressed by protrusions extending from a lower surface of the rotatable disk.

FIGS. 10A and 10B are, respectively, a perspective view and exploded perspective view of the external control unit of the present invention disposed above an implantable device implanted within an eye.

FIG. 11 is a detail view showing the location of the position sensor relative to the implantable device.

IV. DETAILED DESCRIPTION OF THE INVENTION

The ocular drainage system of the present invention comprises an implantable device having a valve that may be non-invasively adjusted to control the resistance to flow of aqueous humor from the anterior chamber of the eye, through the valve, and to a sink outside the eye (e.g., a bleb formed under a scleral flap). The ocular drainage system further comprises an external control unit that permits a health care provider to periodically adjust the valve within the implantable device to maintain intraocular pressures within a desired range, thereby reducing the risk of damage to the optic nerve. In accordance with the principles of the present invention, the valve may be periodically adjusted without requiring re-operation, and includes a simplified flow path that reduces the risk of clogging due to proteinaceous buildup.

An ocular drainage system constructed in accordance with the principles of the present invention is expected to provide a number of advantages over the prior art devices and methods, including:

noninvasive adjustment of fluidic resistance of the shunt over a wide range of values, thereby enabling intraocular pressure to be maintained within desired limits over extended periods of time;

the ability to provide patient-specific adjustments with a simple office visit to a clinician, by which the implantable device may be readily adjusted to apply high fluidic resistance in the early days/weeks postsurgery to avoid hypotony;

the capability to lower resistance of the shunt over the long term to compensate for increased resistance due to fibrosis at the outlet port; and simple internal mechanisms within the implantable device having with few moving parts, so that the implantable device remains functional and adjustable over extended periods of time.

Implantable Device

Figure 1A:
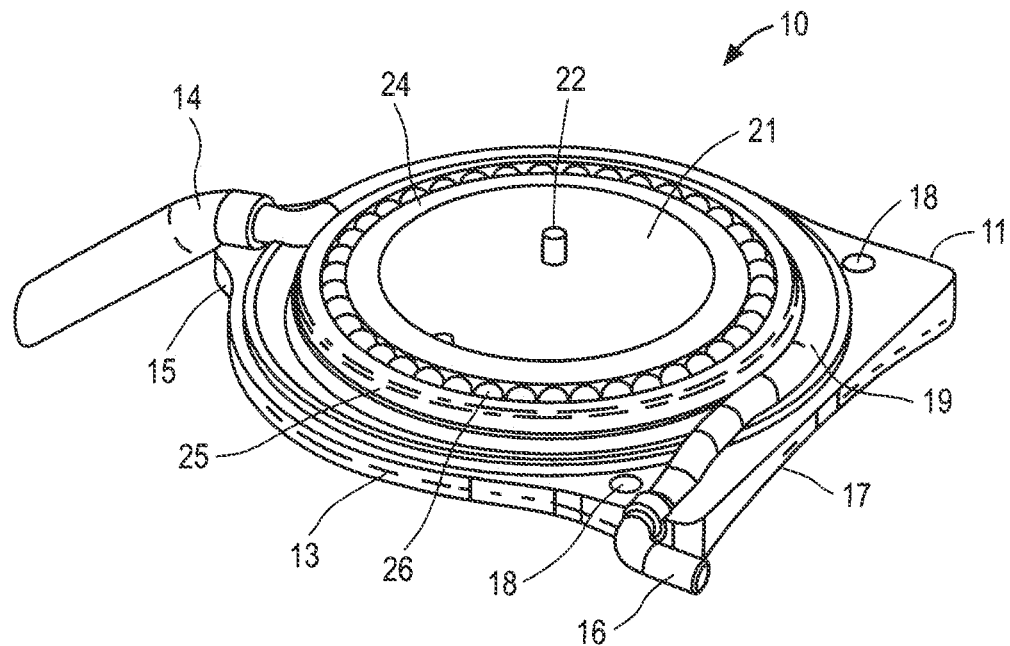
Figure 1B:
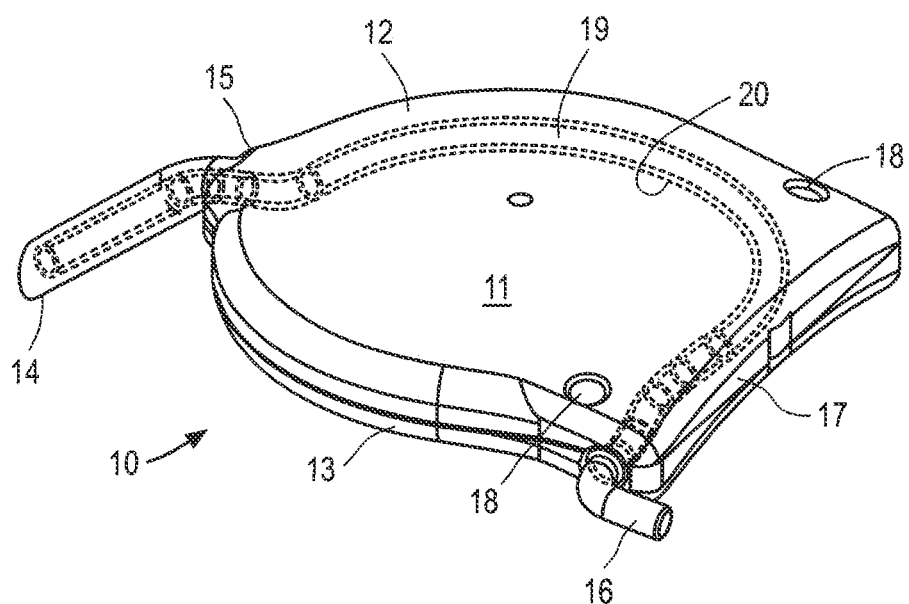
Figure 1C:
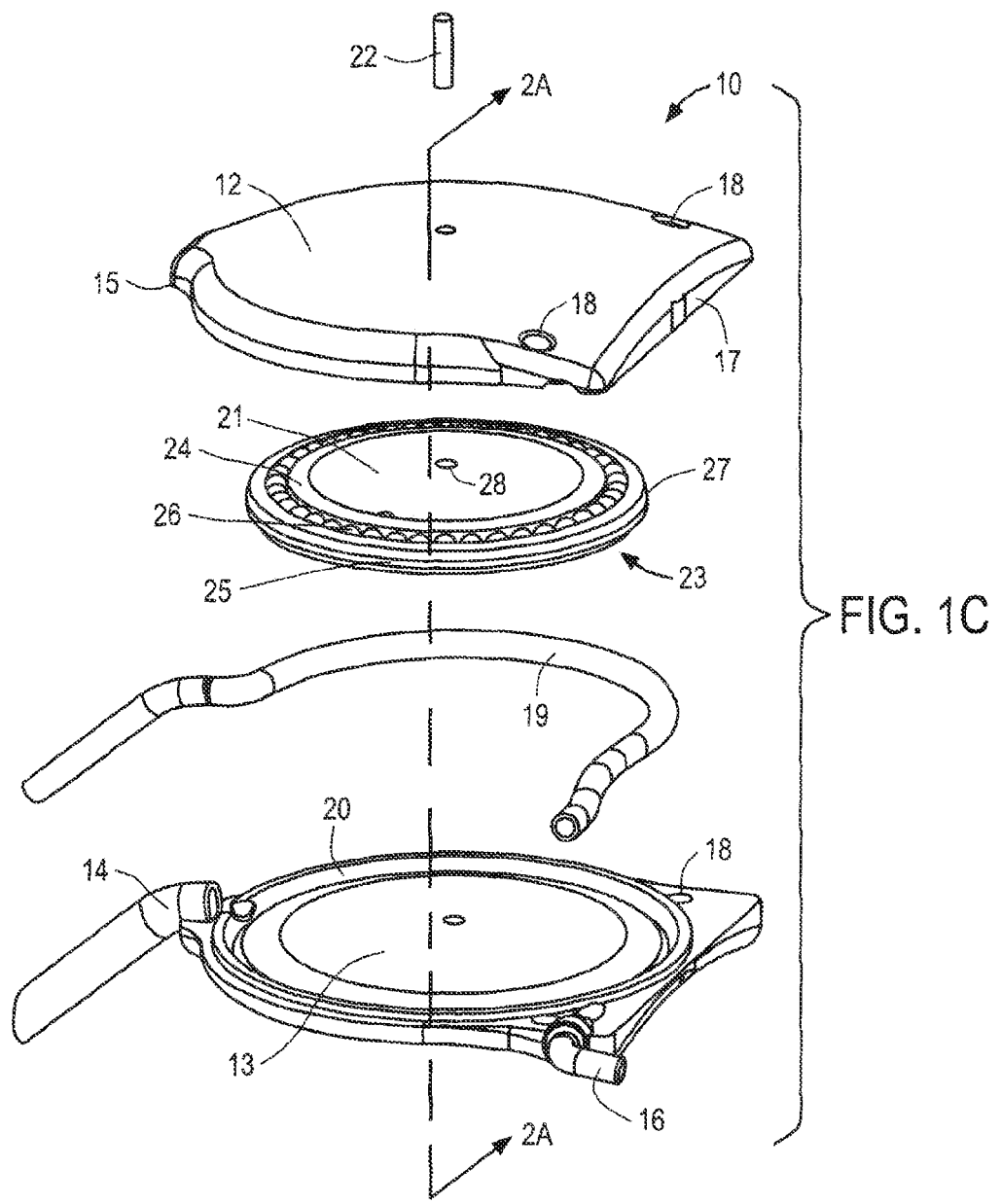

Referring to FIGS. 1A, 1B and 1C, an exemplary embodiment of the implantable portion of the ocular drainage system of the present invention is described. Implantable device 10 comprises housing 11 having upper portion 12 (for clarity omitted from FIG. 1A) and lower portion 13. Inlet port 14 extends from proximal exterior face 15 of housing 11, while outlet port 16 is disposed near distal face 17 of lower portion 12. Inlet port 14 is configured to extend through the wall of the eye and into the anterior chamber when housing 11 is implanted beneath a flap formed in a patient's sclera. Housing 11 preferably includes eyelets 18 that enable the implantable device to be suture to the sclera to retain housing 11 in position once implanted. Fixing the implantable device with respect to the eye is important for measuring the relative position of disk 21 using the external control device, as described in further detail below.

Deformable tube 19 has a central lumen, a flow area and a corresponding fluidic resistance in its undeformed state. Deformable tube 19 extends within housing 11 and is coupled to, or extends through, inlet port 14 and outlet port 16. In a preferred embodiment, outlet port 16 is disposed at an angle of about 45° to the axis of symmetry of the implantable device (e.g., at an angle of about 225° from inlet port 14) to facilitate connection of the outlet port to a Seton tube, such as a Baerveldt or Molteno device). Deformable tube 19 is seated in groove 20 that extends along the circumferences of upper portion 12 and lower portion 13 of the housing 11 between inlet port 14 and outlet port 16.

Disk 21, which may comprise a magnetic or magnetizable material, is disposed within housing 11 on axle 22, and carries ball bearing 23 formed by inner ring 24, outer ring 25 and plurality of balls 26 captured therebetween. Ball bearing 23 ensures that the torque required to rotate the disk remains to throughout the expected useful lifetime of the implant. Outer edge 27 of outer ring 25 bears against deformable tube 19. In one embodiment, axle 22 is disposed through non-concentric opening 28 of disk 21, so that edge 27 of outer ring 25 traces an eccentric path when disk 21 rotates on axle 22. In addition, in the embodiment of FIGS. 1-3, axle 22 is located eccentrically relative to an axis of symmetry of housing 11. In this manner, rotation of disk 21 causes outer edge 27 of bearing 23 to apply to cam force to deformable tube 19, such that the amount of deformation of deformable tube 19 corresponds to the angle of rotation of disk 21.

Disk 21 preferably comprises a permanent magnet having separate poles, and a distinct axis, lying on the plane of the disk that can be sensed using a magnetic sensor. Suitable materials for disk 21 include alloys of SmCo or NdFe. As should be appreciated, non-concentric opening 28 for axle 22 is placed in disk 21 so that the magnetic axis of the disk is aligned with a preferred orientation of the disk when assembled with the other components of the implantable device, for the purposes described below. Deformable tube 19 may comprise a resilient, deformable biocompatible tubing, such as silicone, polyethylene or nylon. Alternatively, as described below, a plurality of deformable tubes may be coupled between inlet port 14 and outlet port 16, such that angular movement of disk 21 compresses and closes off a corresponding subset of deformable tubes. Housing 11 preferably is less than about 6 mm in diameter, and comprises biocompatible, waterproof or water-resistant plastic such as polyether ether ketone ("PEEK") or polycarbonate. The use of PEEK or simpler polymer is particularly desirable, as it provides long-term structural stability when implanted while also allowing for magnetic coupling between disk 21 of implantable device 10 and the magnetic field created by the external control unit, as described below. Ball bearing 23 may comprise a non-magnetic metal alloy or ceramic material, or alternatively may be made out of rubies or similar materials.

Figure 2A:
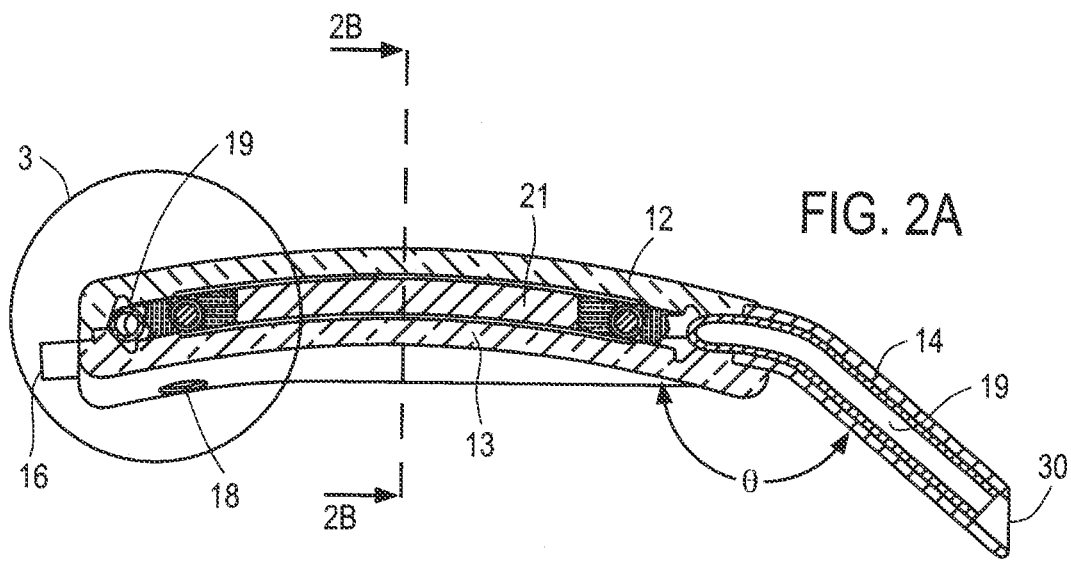
FIGS. 2A and 2B are, respectively, a side sectional view of the implantable device of FIG. 1 taken along the view line 2A-2A and a sectional view taken along view line 2B-2B of FIG. 2A.
Figure 2B:
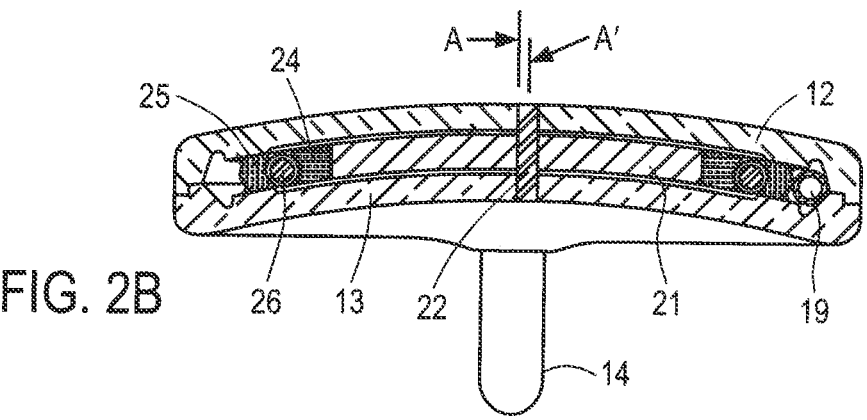
Figure 3:
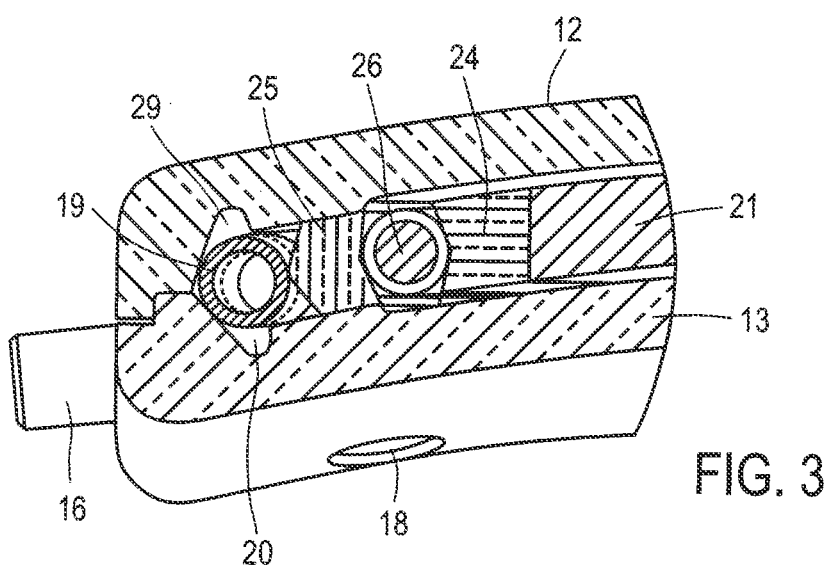
FIG. 3 is a detail view of a portion of the implantable device as indicated in FIG. 2A.

Referring now to FIGS. 2A, 2B and 3, further details of the components of implantable device 10 are described. FIG. 2A is a view of implantable device 10 taken along view line 2A-2A of FIG. 1B, along a plane that coincides with axis of symmetry of housing 11. Consequently, eccentrically located axle 22 is not visible in FIG. 2A. FIG. 2B provides a view at a 90° angle to that shown in FIG. 2A, and therefore passes through axle 22. As depicted in FIG. 2B, an axis A' through axle 22 preferably is displaced from the axis of symmetry A of disk 21 and of housing 11, and is thus may be rotated to a position closer to the side of the housing carrying deformable tube 19. Alternatively, axle 22 may be placed concentrically within housing 11, but instead disk 21 may have an eccentric shape so as to progressively deform deformable tube 19 when rotated about axle 22. FIG. 3 provides a magnified view of the components within call-out 3 of FIG. 2A.

Implantable device 21 is in general configured to be implanted within a scleral flap, as commonly currently used in glaucoma filtration surgery. The human eye is a spherical object having a radius of curvature of approximately 11 mm. Although the implantable device may be fabricated as a totally flat device, it is advantageous to have housing 11 respect the natural radius of curvature. Preferably, housing 11, disk 21 and ball bearing 23 all are constructed to have a curvature that approximates that of the human eye, so that implantable device 10 will lie snugly against the exterior of the eye, or beneath a scleral flap. In particular, implantable device 10 preferably is designed with a consistent curvature, such that the radius of curvature of the lower portion 13 of housing 11 is in a range of about 10 mm to about 12 mm, an more preferably about 11 mm. To achieve minimal thickness for the implantable device, disk 21 also should have the same curvature, as illustrated in FIGS. 2A and 2B.

Still referring to FIG. 2A, to facilitate the introduction of inlet port 14 into the anterior chamber of the eye, inlet port 14 may include rigid nozzle 30 connected to proximal face 15 of housing 11. Nozzle 30 may have a conical or sharpened extremity to facilitate piercing of the scleral tissue and introduction into the anterior chamber. Deformable tube 19 either may be placed tightly and hermetically within nozzle 30, as depicted in FIGS. 1A and 2A, or may be connected in series to nozzle 30. Nozzle preferably is inclined at angle θ with respect to the plane of lower portion 13 of housing 11 to facilitate anatomical placement of the implantable device within a scleral flap and insertion of nozzle 30 into the anterior chamber. Angle θ is selected to ensure that nozzle 30 does not contact or interfere with the iris when implanted, and preferably lies in the range of about 120° to 160° and more preferably about 140°.

During radial compression of deformable tube 19, the tube shortens its dimension in the plane of compression and flattens out, thereby increasing its dimension in the perpendicular plane. To facilitate the compression and deformation of deformable tube 19, grooves 20 and 29 are formed in lower portion 13 and upper portion 12, respectively, of housing, as depicted in FIG. 3. Grooves 20 and 29 accommodate lateral expansion as tube 19 flattens during radial compression, thereby reducing the resistance of tube 19 to deformation and consequently, reducing the torque required to turn disk 21 through a selected angle to compress and deform tube 19.

Figure 4:
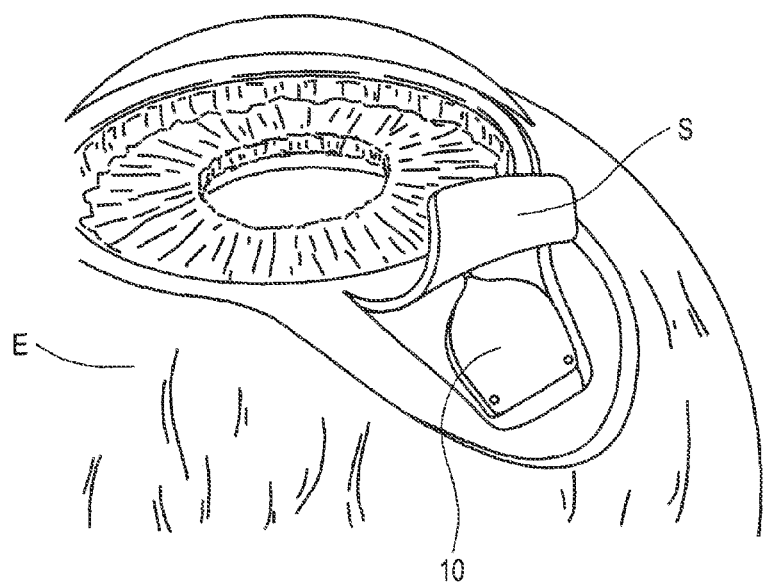
FIG. 4 is a perspective view of the implantable device of the present invention during implantation under a scleral flap formed on the exterior of a patient's eye.

Implantable device 10 is configured to be implanted within eye E, e.g., under a scleral flap S, in a manner similar to other glaucoma drainage devices, as depicted in FIG. 4. Inlet port 14 drains aqueous humor from the interior of the eye, typically the anterior chamber, through deformable tube 19, to the exterior of the eye, typically inside a cavity formed by the scleral flap cavity. In accordance with the principles of the present invention, the rate of drainage, and consequently, the intraocular pressure (IOP), depends on the fluidic resistance of deformable tube 19. This resistance may be adjusted by varying the degree of compression applied to deformation tube 19 by edge 27 of outer ring 25 by rotating disk 21 an axle 22, thus, e.g., reducing the flow area within the tube. Due to the eccentric location of axle 22 relative to the center of disk 21, the amount of compression applied by outer edge 27 of ball bearing 23 is a function of the angular position of disk 21.

Figure 5A:
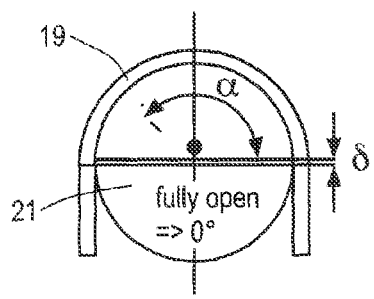
FIGS. 5A to 5E are schematic diagrams showing the amount of constriction imposed on the flow path corresponding to rotation of the disk within the implantable device through selected angles $\alpha$.
Figure 5B:
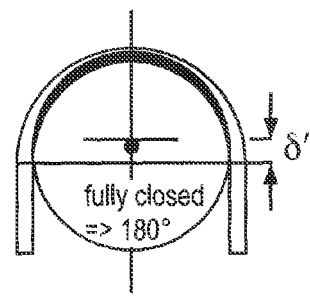
Figure 5C:
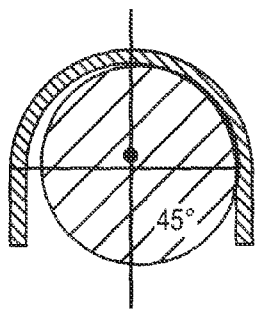
Figure 5D:
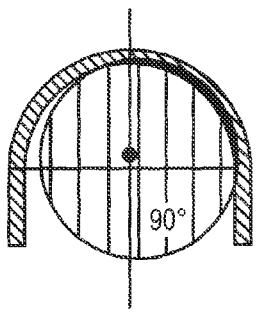
Figure 5E:
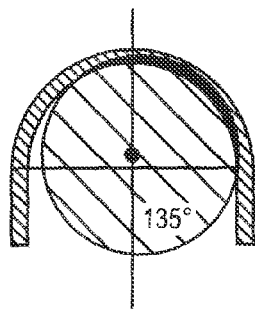

Referring now to FIGS. 5A to 5E, the angular position of disk 21 defines the extent of the zone of the tube that is compressed (shown by the darkened areas in the figures) as well as the level of compression of the tube (shown by the relative thickness of the darkened areas in the figures). FIG. 5A depicts the situation where disk 21 is at a position where angle α is 0°, corresponding to the diameter of disk 21 being parallel to the diameter of housing 11, and offset distance δ from the side of the housing containing deformable tube 19. In this position, disk 21 applies a minimum compressive force to deformable tube 19. FIG. 5B depicts the situation where disk 21 is at a position where angle α is 180°, corresponding to the diameter of disk 21 again being parallel to the diameter of housing 11, but in this case being offset distance δ' towards the side at the housing containing deformable tube 19. In this position, disk 21 applies the maximum compressive force on the tube. FIGS. 5C through 5E depict selected intermediate angles of α at 45°, 90° and 135°, corresponding to rotation of disk 21 through 45 increments that create progressively greater constriction of deformable tube 19. In this manner, compression of deformable tube 19 may be adjusted to provide a wide range of flow restriction.

In addition, aqueous humor drained from the eye flows only through the interior of deformable tube 19, while compressive force is applied to the exterior of the deformable tube. This configuration ensures that proteinaceous materials contained within the aqueous humor passing through the valve cannot create deposits on the working parts of the adjustable valve, and reducing the risk of component failure and blockage of the implantable device.

In principle, disk 21 may be configured to act directly on deformable tube 19 such that ball bearing 23 is entirely omitted, and such a configuration represents one possible embodiment of the implantable device. However, depending on the material of which tube 19 is made, it is possible that friction and/or wear imposed on the tube by repeated adjustment of disk 21 may pose a potential failure mechanism. Accordingly, in the preceding embodiments, ball bearing 23 is employed to reduce shear forces applied to the exterior of deformable tube 19. In addition, ball bearing 23 advantageously reduces the torque required to turn disk 21. In the embodiments depicted in FIGS. 1 through 3, inner ring 24 and outer ring 25 of ball bearing 23 are especially shaped to yield a concave space there between, which confines plurality of balls 26, as shown in FIG. 3. When disk 21 is turned, inner ring 24, coupled to disk 21 turns and balls 26 roll. However, outer ring 25 need not rotate, but rather simply moves radially due to the eccentricity of the disk 21. The configuration of the embodiment depicted in FIGS. 1-3 therefore causes radial movement of outer ring 25 to compress deformable tube 19, while the absence of circumferential motion of the outer ring eliminates friction on the tube, thereby reducing torque and wear.

The proximal end of deformable tube 19, i.e., that extends to the exterior of the eye, may exit housing 11 via a hermetic seal, thus yielding a single outflow point, as shown in the embodiments of FIGS. 1 to 3. However, because fibrotic tissue often forms within the scleral flap and around an implanted device, outlet port 16 of the implantable device may be become partially blocked, thus increasing thus the effective fluid resistance of the tube. In addition, the preceding embodiments may exhibit strong nonlinear dependence of the fluidic resistance on the level of compression of the deformable tube, thereby limiting the useful angular positions of the disk. An alternative embodiment that is expected to resolve these potential issues, and to provide a more linear response of the fluidic resistance as a function of the angular position of disk 21, is described with respect to FIGS. 6A to 6C.

In FIGS. 6A to 6C, an alternative embodiment of the implantable device of the present invention is described, in which like primed numbers are used to indicate similar components as described above for the embodiment of FIGS. 1 to 3. Thus, for example, implantable device 10' of FIG. 6A corresponds to implantable device 10 of FIG. 1A, housing 11' corresponds to housing 11, etc. Implantable device 10' differs from implantable device 10 in that (i) inlet port 14' extends from the surface of lower portion 13', (ii) outlet port 16 is arranged an angle of about 180° from inlet port 14' and comprises a plurality of holes 31 formed in the proximal end of deformable tube 19', (iii) ball bearing 23 (including inner ring 24, outer ring 25 and balls 26) are replaced by variable thickness rim 27' and Bellville spring 32 is employed to tension disk 21' against in movement.

Holes 31 disposed in millet port 16' increase the number of exit points for fluid passing the adjustable valve, and increase the diffusion area, thereby facilitating the outflow from implantable device 10', even in event that fibrotic tissue grows around the implantable device after implantation. Belleville spring 32 applies a preload to disk 21' such that a predetermined minimum torque is required to turn disk 21'. Thus, Belleville spring 32 ensures that disk 21 does not move inadvertently due to normal eye activity, or mechanical shocks such as are encountered during normal human activity. Alternatively, disk 21' and the mating surface of upper portion 12' or the lower portion 13' of housing 11' may include interacting features, e.g., ridges, that lock the disk in position to prevent inadvertent movement of the disk, e.g., due to shock, and which require the application of a minimum threshold of torque adjust the rotation of disk 21'.

Further in accordance with the principles of the present invention, variable thickness rim 27' is designed to overcome potential limitations arising from use of an eccentrically mounted circular disk, as in the embodiment of FIGS. 1-3. In particular, the eccentrically mounted disk 21 of FIGS. 1-3 is symmetric with respect to the angular position of maximum deformation of the tube (180 degrees) as depicted in FIGS. 5A-5E; that is, angular orientations of 135 degrees and 225 degrees produce the amount of compression in deformable tube 19. In order to address this concern, rim 27' of the embodiment of FIG. 6C includes a non-uniform radial thickness Th that provides a camming action as disk 21' is rotated. By choosing an appropriate angular distribution of the variable radial thickness Th of rim 27', it is expected that a more linear increase of the hydraulic resistance as function of angular position may be obtained, thereby enabling the range of useful angular orientations of the disk 21' to be expanded. As shown in FIG. 6C, rim 27' may be affixed directly to the outer edge of disk 21'. Alternatively, however, a ball bearing construction may be employed to provide some of the other advantages discussed above, such as reduced friction.

As a further alternative, instead or, or in addition to, including variable thickness rim 27' on magnetic disk, groove 20' of the embodiment of FIGS. 6A-6C could be formed in the interior of housing 11' so that it is not concentric with respect to disk 21', but instead has a decreasing radius at higher angular orientations of disk 21'. In this case, it is expected that adjusting the angular orientation of disk 21' will cause additional compression of deformable tube as the enlarged portion of variable thickness rim 27' approaches the radially closer portion of groove 20'.

The implantable device of the present invention may be inserted in a scleral flap to regulate drainage of excess intraocular fluid, and thereby regulate IOP in patients afflicted with glaucoma. Aqueous humor passing through the deformable tube and outlet port of the implantable device may exit through the outlet port into the space under the scleral flap, where it will be absorbed by the scleral tissue. More particularly, the fluid will be drained primarily to the connecting vein network. Alternatively, a surgeon may make a second scleral flap with a large cavity beneath it (a bleb) and then make a channel to connect the scleral cavity holding the implantable device to the second cavity. In this case, aqueous humor exiting the outlet port will flow via the channel to the second cavity, where it will be absorbed.

Referring now to FIG. 7, a further alternative embodiment of an ocular drainage system constructed in accordance with the principles of the present invention is described, in which implantable device 10 is connected in series to Seton tube 34, such as a Baerveldt or Ahmed-like glaucoma drainage device by elongated tube 35. In the embodiment of FIG. 7, the outlet port of implantable device 10 is connected to the inflow port of Baerveldt tube 34, e.g., such as the Baerveldt® BG 103-250 Glaucoma Implant available from Abbott Medical Optics, Inc., Abbott Park, Ill., or other similar device.

With respect to FIG. 8, yet another embodiment of an implantable device constructed in accordance with the principles of the present invention is described. Implantable device 40 includes housing 41 having upper portion 42 and lower portion 43. Inlet port 44 extends from the proximal exterior face of housing 41 and is in fluid communication with outlet 46 via an internal lumen of elastically deformable tube 49. Disk 51 rotates concentrically about axle 52, and includes variable thickness rim 53 that serves to provide a camming action as described hereinafter. Plurality of movable pins 54 are disposed in radially oriented slots 55 formed in housing 41, and are arranged to reciprocate within slots 55 in response to cam forces applied by variable thickness rim 53 and elastic recovery forces of deformable tube 49. Accordingly, when disk 51 is rotated through predetermined angles about axle 52, different ones of the plurality of movable pins 54 are urged against deformable tube 49, thereby progressively reducing the flow area, and increasing the fluidic resistance of, implantable device 40. Depending on the local thickness of rim 53, movable pins 54 will be pushed at variable degrees along their respective slots and will, correspondingly, compress deformable tube 49.

Movable pins 54 preferably have rounded ends to minimize friction with variable thickness rim 53 and also to provide a rounded compression surface on deformable tube 49. The number of movable pins may be selected as a matter of design choice, although with higher numbers of movable pins, higher angular resolution may be obtained in adjusting the effective hydraulic resistance of implantable device 40. Advantageously, the embodiment of FIG. 8 is expected to provide a wider range of adjustment of fluidic resistance, higher precision in compressing deformable tube 49, and the concentrically mounted construction of disk 51 is expected to be easier to manufacture than the eccentric axle designs described in FIGS. 1 and 6.

Referring now to FIG. 9, yet another exemplary embodiment of the implantable device of the present invention is described. Implantable device 60 includes a housing similar to those depicted in FIGS. 1, 6 and 8 (only lower portion 61 being shown in FIG. 9). Implantable device 60 differs from preceding embodiments in that, instead of having a single deformable tube disposed in a groove along the periphery of the housing, inlet 62 is coupled to outlet 63 by a plurality of separate deformable tubes 64. In addition, rather than being configured so that an outer perimeter of an angularly adjustable disk bears against the deformable tube, the disk instead includes a plurality of protrusions 65 extending from its lower surface. Protrusions 65 are arranged on the disk so that partial rotation of the disk brings different ones of the protrusions into contact with, and compresses, selected ones of the plurality of deformable tubes 64. This in turn enables the total flow area through implantable device 60, and thus the fluidic resistance, to be readily adjusted by changing the orientation of the disk within the housing of the implantable device, for example, using the external control units described below.

Because the resistance of the network of deformable tubes 64 depends on the number of tubes running in parallel between inlet 62 and outlet 63, and on the resistance of each tube, by selectively occluding different ones of the tubes at different angular positions, the embodiment of FIG. 9 also provides a large number of functional positions having distinctly different resistances. The size of each deformable tube 64 and the disposition of each protrusion 65 preferably will be selected so that when rotating the disk in one direction (i.e., counterclockwise) the resistance will increase or decrease in a consistent and quasi-linear fashion. As an example, in the specific angular position of the disk shown in FIG. 9, two protrusions 65 occlude the two far right deformable tubes 64. So in this particular configuration, the resistance of the tube is determined by the sum of the resistances of the three deformable tubes 64 that remain open.

External Control Unit

Referring now to FIGS. 10A, 10B and 11, an exemplary embodiment of the external control unit of the ocular drainage system of the present invention is now described. In each of the figures, control unit 70 is shown disposed above and spaced apart from implantable device 10 of the present invention. In one embodiment control unit 70 comprises housing 71 containing position sensor 72, electromagnet 73, actuator 74. Control unit 70 also may include a display, or may be configured to be coupled to optional conventional processing and display system 90, e.g., a suitably programmed personal or laptop computer, using a cable or wirelessly using, e.g., an IEEE 802.11 compliant wireless chip. As will be readily appreciated, control unit 70 and processor and display system 90 are not to scale.

As depicted in FIG. 10B, control unit 70 is configured to be positioned above a patient's eye E so that position sensor may determine the angular orientation α of disk 21 within implantable device 10 and generate an output signal for display on processing and display system 90. Electromagnet 73 provides magnetic coupling between the disk within implantable device 10 and the external control unit, so that using actuator 74, a health care provider may adjust the angular orientation α of disk 21 within the implantable device. Any corresponding movement of the disk, corresponding to an adjustment of the amount of compression of deformable tubing 19 within the implantable device, is sensed by position sensor 72 and displayed on control unit 70 or processing and display system 90.

As depicted in FIGS. 10A and 11, position sensor 72 preferably is mounted on circuit board 75 suspended on sensor stalk 76, such that position sensor 72 is disposed in close proximity to, but not touching, implantable device 10 during the adjustment process. In this embodiment, position sensor 72 is a magnetic sensor, and is configured to sense the angular orientation of the disk disposed within the implantable device when electromagnetic 73 is de-energized. As discussed above, disk 21 has a distinct magnetic axis which can be sensed by position sensor 72 to determine the angular orientation α of the disk.

Electromagnet 73 comprises proximal magnet core 78, main magnetic core 79 and distal magnetic core 80. Electric coils 81 surround main magnetic core 79 and induce a magnetic field within magnetic cores 78, 79 and 80, using methods that are know in the art. The magnet field generated at proximal magnetic cores 78 magnetically couples the disk in the implantable device to control unit 70. Control unit 70 further comprises rods 82, the lower ends of which support bottom cover 83 and the upper ends of which are connected to distal magnetic core 80. Holes 84 in bottom cover 83 allow proximal magnetic cores 78 to pass through the bottom cover so that core 78 can be disposed in proximity to the implantable device. Preferably, the strength of the magnetic field that couples the disk within the implantable device to the control unit results in a force that is tolerated by the scleral tissue, e.g., less than 1 Newton. In one embodiment, the disk and external control unit each have a magnetic field strength of about 0.8 Tesla, such that it maximum torque of about 1.2 mNm can be applied to the disk, while the estimated vertical force is less than about 0.12 N.

Actuator 74 may comprise either a manual crank or electric motor, and is configured to make adjustments in the angular orientation of the disk 21 of the implantable device when magnetically coupled to control unit 70. In one embodiment, actuator 74 comprises an electric motor that is coupled to distal magnetic core and configured to rotate electromagnet 73 within housing 71. As should be appreciated, housing 71 may be held in the physician's hand, but more preferably is mounted on a rigid support arm that can be positioned within a predetermined distance of the patient's eye. Actuator 74 may in addition be coupled to processor and display system 90, and actuated using software resident on processing and display system 90 to fine tune adjustment of the implantable device.

Control unit 70 is used to perform two principal tasks as set out in the following paragraphs: (1) sensing the relative angular position of disk 21 within the implantable device (which defines the operational position of the implantable device) and (2) rotating disk 21 within the implantable device, either clockwise or counterclockwise, by selected amount to adjust the flow resistance of the implantable device. As noted above, control unit 70 preferably is mounted fixed in space, for example, suspended above an examination chair in the health care provider's office.

A method of using control unit 70 to adjust the fluidic resistance of the implantable device of the present invention is now described. For a patient in whom an implantable device was previously implanted, a first step of the method may include measuring the patient's intraocular pressure, e.g., using tonometry. Next, the patient may be seated, for example, in and examination chair accessible to control unit 70. If the implantable device were previously implanted under a scleral flap along a meridional plane of the eye, just above the iris, the patient may be instructed to look straight down to expose the implant. The control unit may be moved into position at a selected distance above the patient's eye, for example, using a motorized or manually-adjusted articulated support arm.

Next, position sensor 72 measures the location of the magnetic axis of the disk within the implantable device, and its orientation is displayed on processor and display system 90. While electromagnet 73 is de-energized (i.e., no current in the coils), the health care provider manually or automatically rotates the internal mechanism of control unit 70 so that the edges of the anus of proximal magnetic cores 78 are concentric with, and aligned with, the magnetic axis of disk 21 within the implant, as may be determined using the output of the magnetic sensor. This may be facilitated by including a camera on control unit 70, such that the orientation of the magnetic axis of the disk of the implantable device may be superimposed on a real-time image of the patient's eye that includes the arms of proximal magnetic cores 78.

Once the control unit is properly aligned with the implant, electromagnet 73 is energized to induce a magnetic field that passes through the anus of proximal magnetic cores 78 having opposite polarity to that of the magnetic fields of disk 21, thereby producing a strong phase lock that aligns disk 21 to the external magnetic field created by control unit 70. As should be appreciated, the magnetic field induced by electromagnet 73 is the direction of the line passing through the tips of the arms of proximal magnetic cores 78. Once the phase lock is established, and while keeping the electromagnetic system energized, the health care worker executes a desired rotation of the proximal magnet cores 78 using actuator 74. Because disk 21 within the implantable device is phase locked to the external magnetic field, it will remain aligned to the external field and will simultaneously undergo the same rotation within the implantable device. As discussed above, the external magnetic field created by electromagnet 73 is sufficiently strong to apply the torque required to turn the disk within the implantable device, for example, to overcome the preload applied by the locking feature (e.g., Belleville spring), if present, and any frictional resistance.

After actuator 74 has turned the disk through the desired amount, electromagnet 73 is de-energized, and position sensor 72 is employed to check the relative rotational position of the disk within the implantable device to verify that the intended rotation has indeed taken place. After allowing a suitable period for pressure to equilibrate within the eye at the new valve setting, the health care provider may again check intraocular pressure within the patient's, e.g., using tonometry.

Figure 12:
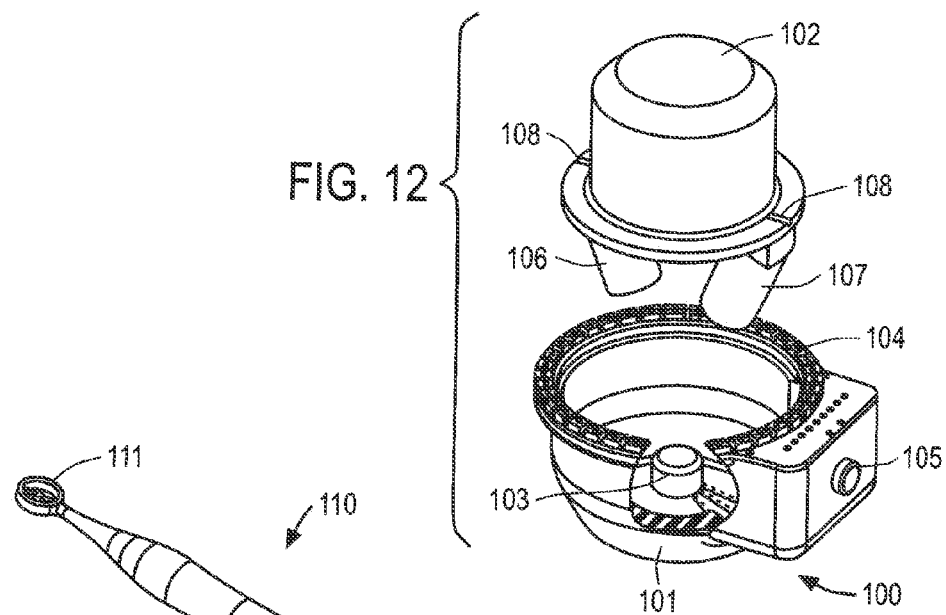
FIG. 12 is a perspective view of an alternative embodiment of the an external control unit of the present invention.

Referring now to FIG. 12, an alternative embodiment of an external control unit is described. External control unit 100 is a more compact, less complicated and user-friendly version of the embodiment of FIGS. 10 and 11. External control unit 100 permits the health care provider to perform two essential functions with respect to the implantable device described herein above: (1) measure the functional position of the disk within the implantable device; and (2) perform noninvasive adjustment of the detected functional position, thereby adjusting the drainage characteristics (fluidic resistance) of the implantable device.

External control unit 100 comprised of two main parts, sensor display unit 101 and an adjustment unit 102. Sensor display unit 101 is configured to be positioned on top of a patient eye's, directly above the implantable device, and contains sensor 103 for measuring the orientation of the magnetic disk (e.g., disk 21 or 51) within the implantable device. Sensor display unit 101 also includes array 104 of LEDs disposed circularly on its periphery to display the measured angular position of the magnetic disk using electronics activated by button 105.

Adjustment unit 102 is designed to be positioned coaxially within sensor display unit 102, and contains a magnet having poles 106 and 107 that creates a strong magnetic field in the vicinity of the implantable device. When positioned within sensor display unit 101, poles 106 and 107 of magnet in adjustment unit 102 may be aligned in opposite polarity to the poles of the magnetic disk of the implantable device, whereby a strong magnetic coupling may be achieved. When adjustment unit 102 is disposed within sensor display unit 101, position marks 108 should be aligned with the LEDs corresponding to the magnetic disk orientation sensed by sensor 103. Subsequent rotation of adjustment unit 102 induces an equivalent rotation of the magnetic disk of the implantable device, thereby adjusting its functional position and the resulting fluidic resistance of the implantable device.

Further details regarding implantation of an implantable device as described hereinabove are now provided. The implantable device (e.g., device 10, 10', 40 or 60) is implanted using a surgical technique similar to that used for prior art glaucoma drainage devices. As depicted in FIG. 4, a scleral flap is created in a manner analogous to standard trabeculectomy, and the flap is dissected carefully up to clear cornea. The scleral flap is lifted and care is taken to identify the center of the "blue zone" adjacent to clear cornea, which corresponds to the location of the trabecular meshwork. As will be understood by one of skill in the an the "blue zone" is located posterior to the anterior limbal border, and terminates in midlimbal line. A 26-gauge needle is inserted into the anterior chamber through the center of the "blue zone" at an angle parallel to the iris plane. The inlet port of the implantable device then is inserted all the way into the anterior chamber through the ostium created by the needle. The implantable device is secured in place within the scleral flap by applying sutures through the two eyelets provided (e.g., eyelets 18 in FIG. 1B). The scleral flap is then sutured in place using a 10-0 nylon suture with a spatulated needle. Finally the conjunctiva is carefully closed by appropriate suturing.

Once the implantable device is implanted as described above, the angular orientation of the magnetic disk may be adjusted using the external control unit to adjust the fluidic resistance of the implantable device. The adjustment procedure using the external control unit of FIG. 12 includes steps of (1) measuring the functional position of the magnetic disk prior to adjustment; (2) adjusting the functional position of the magnetic disk and (3) measuring and verifying the functional position of the magnetic disk after the adjustment.

The foregoing procedure starts by placing sensor display unit 101 on top of the patient's eye, which is kept still and in a position to best expose the implant. Sensor display unit 101 is placed in relation to the eye so that sensor 103 is just above the implantable device. The operator then depresses button 105, which causes sensor 103 to measure of the orientation of the magnetic field created by the magnetic disk of the implantable device. Electronics in sensor display unit read the output sensor 103 and identify the magnetic field orientation by lighting two diametrically opposed LEDs of LED array 104, so that a fictitious line between the two illuminated LEDs matches the direction of the magnetic field. The polarity of the magnetic field also may be displayed by using appropriate LED colors, i.e., red color for North and green for South.

Once the direction of the magnetic disk is identified and displayed on sensor display unit 101, the operator places adjustment unit 108 coaxially within sensor display unit 101 taking care that poles 106 and 107 of the adjustment unit are perfectly aligned and in opposite polarity to the magnetic field of the implantable device, as indicated on LED array 104. This is facilitated by two color position marks 108, indicating the N (green dot) and S (red) pole of the adjustment unit, which are placed permanently and in diametrically opposite positions on the periphery of the adjustment unit, as shown in FIG. 12. Aligning position marks 108 to the same colored LEDs on sensor display unit 101 ensures that the two magnets are strongly coupled magnetically and any rotation of the adjustment unit will entrain an equivalent rotation of the magnetic disk within the implantable device. The operator then is free to rotate adjustment unit 102 clockwise or counterclockwise (while sensor display unit 101 is held fixed) to either increase or decrease the functional position of the magnetic disk, and thus the fluidic resistance of the implantable device.

Once the foregoing adjustment is made, the operator may remove the adjustment unit and depress button 105 to sense and display a new measurement for the magnetic field, and to verify that the magnetic disk has indeed rotated appropriately. This will be the case when the LEDs of sensor display unit 101 and position marks 108 of adjustment unit 102 again are aligned. It should be noted that the inventive system allows for a relative adjustment of the fluidic resistance of the implant, and does not affect a direct adjustment of the intraocular pressure of the eye. Accordingly, after a suitable period to allow the fluid flow through the implantable device to come to equilibrium, the physician should measure IOP after the adjustment using appropriate means (i.e., tonometry) and, if necessary, repeat the adjustment until the desired IOP is achieved.

Figure 13:
FIG. 13 is a perspective view of a further alternative embodiment of an external control unit of the present invention.
Figure 14:
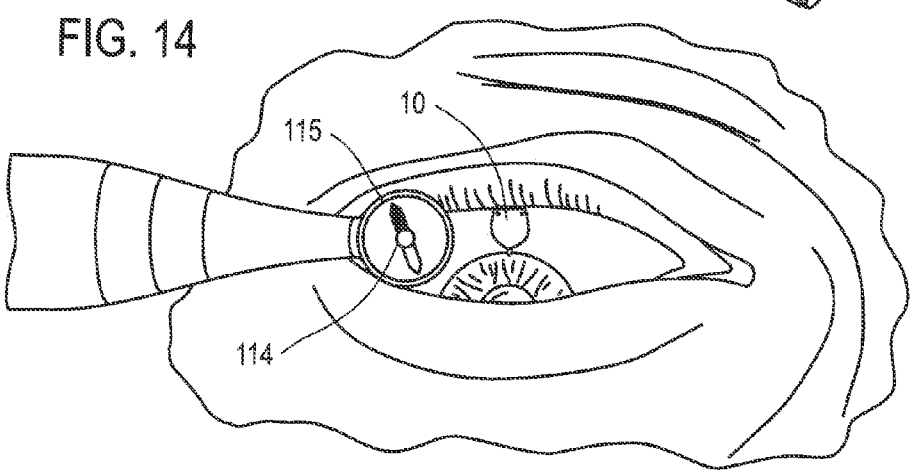
FIG. 14 is a perspective view depicting use of the external control unit of FIG. 13 to first determine the angular orientation of the disk within the implantable device implanted in a patient's eye prior to adjusting the angular orientation of the disk to adjust fluidic resistance of the implantable device.

Referring now to FIGS. 13 and 14, a further alternative embodiment of the external control unit of the present invention is described. External control unit 110 represents a further effort to reduce the complexity of the external control unit to be used with the implantable device of the present invention, such that external control unit 110 comprises a simple pen-like unit. More specifically, external control unit 110 includes flat compass 111 at one end, spirit level 112 and permanent magnet 113 at the other end. Flat compass 111 is provided for measuring the orientation of the magnetic disk within the implantable device. Magnetic needle 114 of compass 111 is colored to indicate the north pole and the transparent cover or the outer rim of housing 115 contains graduations for easier reading of the angular position of the needle. Permanent magnet 113 is disposed on the other end of external control unit 110, and is used for adjusting the angular orientation of the magnetic disk within the implantable device, as described below. Spirit level 112 is disposed in the main body of unit 110 and allows the user (physician) to confirm that the external control unit is in a horizontal position while measuring the magnetic disk orientation, thereby ensuring that a fixed reference frame is provided for all measurements (e.g., before and after each adjustment attempt).

A method of adjusting the fluidic resistance of an implantable device is now described with respect to FIG. 14, and includes steps similar to those described above for the preceding embodiments of external control unit.

First, a measurement of the functional position of the magnetic disk within the implantable device is taken to determine the current angular position of the magnetic disk. With the patient seated and motionless, and with the head in a vertical position (e.g., immobilized against a typical eye examination frame), the physician polls on the eyelid to expose the sclera. Compass 111 is then placed flat on the scleral flap, right above the implantable device, while the physician verifies that unit 110 is in horizontal position using spirit level 112. The angular position of compass needle 114 is noted, which corresponds to the orientation of the magnetic field emanating from the magnetic disk of the implantable device. It is expected that the magnetic disk of the implantable device will create a magnetic field in its vicinity that is orders of magnitudes greater (e.g., 150 times higher) than the magnetic field of the earth. Accordingly, the earth's magnetic field is not expected to interfere with the ability of compass 111 to accurately determine the orientation of the magnetic field of the disk within the implant.

Next, the physician turns unit 110 by 180 degrees so that the magnet (e.g., south pole) is adjacent to the sclera and near the position previously indicated by the north pole of compass 111. Positioning magnet 113 in this manner couples magnet 113 to the magnetic disk of the implantable device. The physician then moves magnet 113 in a clockwise or counterclockwise direction through a circular arc over the implantable device, causing the magnetic disk of the implantable device to rotate accordingly and increase or decrease the hydraulic resistance of the implantable device.

The physician again reverses external control unit 110 to bring the compass adjacent to the implantable device to sense the orientation of the magnetic field emanating from the implantable device. The physician may then repeat the foregoing steps a number of times until the magnetic disk within the implantable device is confirmed to have moved through a desired angle. The physician preferably then performs a measurement of IOP using a tonometer or similar device. As noted above, this test preferably is performed only after IOP is expected to have reached anew steady state (e.g., after approximately 15-30 minutes). If IOP now is within the physiological or desired range, the procedure complete. Otherwise further adjustment may be performed.

Alternative embodiments of the ocular drainage system of the present invention may include a miniaturized pressure sensor disposed with the implantable device and in communication with inlet port 14 to measure intraocular pressure. This sensor may be coupled to a miniaturized telemetry system, such as those based on radio frequency identification principles, that may be energized from distance, e.g., by circuitry on control unit 40, to emit a signal that can be received and interpreted by an external receiver. This arrangement would provide an easy and non-invasive measurement of intraocular pressure.

In further alternative embodiments, disk 21 within the implantable device may comprise a magnetizable material rather than a permanent magnet, and may further include circuitry for inducing a local magnetic field in the disk that is out of phase with the magnetic field applied by control unit 40. In this embodiment, control unit 40 applies an alternating magnetic field to energize the circuitry disposed within the implantable device to generate a local magnetic field of opposite polarity. In this way, the magnetic field supplied by control unit 40 may be employed to generate a local magnetic field, and coupling between those fields may be used to steer the disk within the implantable device to induce a desired degree of rotation. As a yet further alternative embodiment, implantable device 10 may be configured as an ultrasonic motor, in which case control unit 40 is coupled ultrasonically to the disk disposed within the implantable device, rather than employing magnetic coupling.

As a yet further alternative, a plurality of tubes may be substituted for deformable tube 19 within the housing 11. In this embodiment, rotation of the disk within the implantable device selectively and reversibly closes off a corresponding subset of the plurality of tubes, rather than simply deforming a single deformable tube 19.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of adjusting intraocular pressure within an eye, the method comprising:
 introducing aqueous humor into an inlet of a deformable tube disposed within a circumferential groove extending between an inlet port and an outlet port of a housing of an implantable device implanted on or within an exterior layer of the eye so that the deformable tube is in communication with the aqueous humor in an anterior chamber of the eye;
 draining the aqueous humor through the deformable tube at a first drainage rate caused by application of a compressive force on the deformable tube by a disk eccentrically mounted within the housing, the disk positioned at a first stationary position along an arc; and moving the disk within the housing to a second stationary position along the arc to adjust an angular orientation of the disk within the housing such that an adjusted compressive force is applied to the deformable tube causing aqueous humor to move through the deformable tube at a second drainage rate, different from the first drainage rate.

2. The method of claim 1, wherein the second stationary position is 180 or less along the arc from the first stationary position.

3. The method of claim 1, wherein moving the disk comprises non-invasively moving the disk.

4. The method of claim 3, wherein the disk is non-invasively moved using an external control unit.

5. The method of claim 4, further comprising measuring the angular orientation of the disk prior to moving the external control unit.

6. The method of claim 5, further comprising displaying a measured angular orientation of the disk.

7. The method of claim 4, wherein the disk is magnetic and the external control unit comprises a magnet, and non-invasively moving the disk further comprises coupling the magnetic field of the magnet to the magnetic field of the disk.

8. The method of claim 4, wherein the external control unit comprises a magnetic sensor, the method further comprising measuring, via the magnetic sensor, and displaying the angular orientation of the disk prior to moving the external control unit.

9. The method of claim 1, further comprising a step of measuring intraocular pressure within the eye.

10. An ocular drainage system for the treatment of excess fluid within an eye, the system comprising:
a housing comprising an inlet port and an outlet port and a portion defining a circumferential wove that extends therebetween the housing configured to be implanted on or within an exterior layer of the eye;
at least one deformable tube disposed within the groove to provide fluid communication between the inlet port and the outlet port, the deformable tube having at least one lumen; and
a disk eccentrically mounted within the housing, the disk configured to move from a first stationary position along an arc, wherein the disk applies a compressive force on the deformable tube to permit fluid to drain through the deformable tube at a first drainage rate, to a second stationary position along the arc, wherein the disk applies an adjusted compressive force on the deformable tube to permit fluid to drain through the deformable tube at a second drainage rate different from the first drainage rate.

11. The ocular drainage system of claim 10, wherein the second stationary position is 180° or less along the arc from the first stationary position in a clockwise or counterclockwise manner.

12. The ocular drainage system of claim 10, wherein the inlet port further comprises a nozzle configured to pass through a wall of the eye to communicate with aqueous humor in an anterior chamber of the eye.

13. The ocular drainage system of claim 10, further comprising a magnet configured to rotate the disk from the first stationary position to the second stationary position, and
wherein, optionally, the implantable housing further comprises a circuit.

14. The ocular drainage system of claim 10, wherein the implantable housing is adapted to be implanted under a scleral flap,
wherein the outlet port is configured so that fluid exits the outlet port beneath the scleral flap, and
wherein the outlet port comprises a plurality of holes disposed in the deformable tube or the outlet port is configured to be connected to a Seton tube, or both.

15. The ocular drainage system of claim 10, further comprising a ball bearing interposed between the disk and the deformable tube.

16. The ocular drainage system of claim 10, wherein the groove is located at a non-uniform radial distance from the disk.

17. The ocular drainage system of claim 10, further comprising an external control unit configured to non-invasively move the disk from the first stationary position to the second stationary position in a clockwise or counter-clockwise manner via magnetic coupling between the external control unit and the disk.

18. The ocular drainage system of claim 10, wherein the external control unit further comprises a sensor, the system further comprising a processor and display unit for displaying an output of the sensor.

19. The ocular drainage system of claim 10, wherein the disk is configured to move to additional stationary positions along the arc.

* * * * *